(12) United States Patent
Schaller

(10) Patent No.: US 10,888,316 B1
(45) Date of Patent: Jan. 12, 2021

(54) WORK HARDENING OF STAPLES WITHIN SURGICAL STAPLER

(71) Applicant: Aesculap AG, Tuttlingen (DE)

(72) Inventor: Michael P. Schaller, Palo Alto, CA (US)

(73) Assignee: AESCULAP AG, Tuttlingen (DE)

( * ) Notice: Subject to any disclaimer, the term of this patent is extended or adjusted under 35 U.S.C. 154(b) by 116 days.

(21) Appl. No.: 14/946,608

(22) Filed: Nov. 19, 2015

Related U.S. Application Data

(63) Continuation of application No. 12/782,880, filed on May 19, 2010, now Pat. No. 9,192,377.

(Continued)

(51) Int. Cl.
*A61B 17/00* (2006.01)
*A61B 17/064* (2006.01)
(Continued)

(52) U.S. Cl.
CPC .... *A61B 17/0644* (2013.01); *A61B 17/07207* (2013.01); *A61B 19/30* (2013.01);
(Continued)

(58) Field of Classification Search
CPC ............ A61B 17/07207; A61B 17/068; A61B 2017/07278; A61B 2017/07228
(Continued)

(56) References Cited

U.S. PATENT DOCUMENTS 1,746,496 A * 2/1930 Palmgren ................ B25C 5/085
227/86
1,761,640 A * 6/1930 Palmgren ................ B25C 5/085
227/86
(Continued)

OTHER PUBLICATIONS

Cardica Microcutter Implant Delivery Device 510(k), Cover Sheet, Table 10.1, "Substantial Equivalence Comparison," and Section 12, "Substantial Equivalence Discussion", Oct. 18, 2010.

*Primary Examiner* — Robert F Long

(57) ABSTRACT

An exemplary medical apparatus may include a surgical tool; a feeder belt located at least partially within the surgical tool; a plurality of staples affixed to and frangibly separable from the feeder belt; and a forming station positioned within the surgical tool that receives the feeder belt; where motion of the feeder belt through the forming station bends at least one staple relative to the feeder belt substantially at the junction between that staple and the feeder belt in order to work harden that junction within the surgical tool. Another exemplary medical apparatus may include a surgical tool; a feeder belt located at least partially within the surgical tool; staples affixed to and frangibly separable from the feeder belt; and a channel within the surgical tool that receives the feeder belt; where motion of the feeder belt through the channel bends at least one staple at least at one location, thereby work hardening that staple at each location at which it bends. A method for work hardening a portion of a surgical staple may include providing a surgical tool, a feeder belt located at least partially within the surgical tool, and staples affixed to and frangibly separable from the feeder belt; moving the feeder belt relative to the surgical tool; and as a result of that moving, contacting at least one staple with a portion of the surgical tool; and as a result of that contacting, work hardening a part of the staple.

17 Claims, 2 Drawing Sheets

Related U.S. Application Data

(60) Provisional application No. 61/183,376, filed on Jun. 2, 2009.

(51) Int. Cl.
*A61B 17/072* (2006.01)
*A61B 19/00* (2006.01)

(52) U.S. Cl.
CPC ............... *A61B 2017/00526* (2013.01); *A61B 2017/07271* (2013.01); *A61B 2019/307* (2013.01)

(58) Field of Classification Search
USPC ............................... 227/175.1–182.1; 606/219
See application file for complete search history.

(56) References Cited

U.S. PATENT DOCUMENTS

| | | | | |
|---|---|---|---|---|
| 2,174,708 A * | 10/1939 | Sears et al. | ............... | B25C 5/16 227/86 |
| 2,431,812 A * | 12/1947 | Lang | ..................... | B25C 5/085 227/86 |
| 2,880,540 A | 4/1959 | Williams | | |
| 3,117,757 A | 1/1964 | Sampson | | |
| 3,151,443 A * | 10/1964 | Sitzler | .................... | B21D 53/36 59/77 |
| 3,477,089 A | 11/1969 | Aaron | | |
| 3,650,453 A | 3/1972 | Smith, Jr. | | |
| 4,060,089 A | 11/1977 | Noiles | | |
| 4,066,165 A * | 1/1978 | Ruskin | .................... | F16B 15/08 206/340 |
| 4,127,227 A | 11/1978 | Green | | |
| 4,151,944 A * | 5/1979 | Picton | ................... | B25C 5/1624 227/120 |
| 4,204,623 A * | 5/1980 | Green | ................ | A61B 17/0684 227/121 |
| 4,453,661 A * | 6/1984 | Genyk | ................ | A61B 17/072 227/144 |
| 4,570,841 A * | 2/1986 | Olesen | ................... | B25C 5/045 227/120 |
| 4,583,640 A * | 4/1986 | Gillam | ................. | H01R 13/514 206/716 |
| 4,588,121 A * | 5/1986 | Olesen | ................... | B25C 5/045 206/338 |
| 4,589,416 A | 5/1986 | Green | | |
| 4,805,617 A * | 2/1989 | Bedi | .................. | A61B 17/0643 606/220 |
| 4,852,737 A * | 8/1989 | Noll | ..................... | B65D 73/02 206/485 |
| 5,156,315 A * | 10/1992 | Green | ................ | A61B 17/07207 227/178.1 |
| 5,250,058 A * | 10/1993 | Miller | ..................... | A61B 17/11 24/615 |
| 5,303,539 A * | 4/1994 | Neamtu | .................. | B21F 45/24 59/72 |
| 5,385,287 A * | 1/1995 | Scheuten | .................. | B42B 4/02 227/155 |
| 5,398,860 A * | 3/1995 | Edwards | ................. | B21J 15/32 227/119 |
| 5,456,400 A * | 10/1995 | Shichman | ............ | A61B 17/064 227/176.1 |
| 5,490,591 A * | 2/1996 | Faulkner | ................ | B65G 17/08 198/484.1 |
| 5,653,372 A * | 8/1997 | Richardson | ............... | B25C 7/00 227/110 |
| 5,818,186 A | 10/1998 | Camino | | |
| 5,833,695 A | 11/1998 | Yoon | | |
| 5,902,310 A * | 5/1999 | Foerster | ............. | A61B 17/0644 606/142 |
| 5,974,918 A * | 11/1999 | Nakagawa | ............ | B25B 23/045 81/434 |
| 6,050,471 A * | 4/2000 | Yagi | ...................... | B25C 5/1689 227/119 |
| 6,193,129 B1 * | 2/2001 | Bittner | ................. | A61B 17/1114 227/180.1 |
| 6,371,352 B1 * | 4/2002 | Mochizuki | ................ | B27F 7/38 227/120 |
| 6,391,038 B2 | 5/2002 | Vargas et al. | | |
| 6,698,591 B2 * | 3/2004 | Casses | ................... | B65D 73/02 206/713 |
| 6,779,959 B1 * | 8/2004 | Yang | ...................... | B25C 1/184 206/347 |
| 6,877,646 B2 | 4/2005 | Paynter | | |
| 7,604,151 B2 * | 10/2009 | Hess | .................... | A61B 17/105 227/176.1 |
| 7,905,902 B2 | 3/2011 | Huitema et al. | | |
| 7,918,376 B1 | 4/2011 | Knodel et al. | | |
| 7,934,630 B2 | 5/2011 | Shelton et al. | | |
| 7,954,683 B1 | 6/2011 | Knodel et al. | | |
| 7,963,432 B2 | 6/2011 | Knodel et al. | | |
| 7,988,026 B2 | 8/2011 | Knodel et al. | | |
| 8,220,690 B2 | 7/2012 | Hess et al. | | |
| 8,801,732 B2 | 8/2014 | Harris et al. | | |
| 9,155,536 B1 * | 10/2015 | Hausen | ................ | A61B 17/068 |
| 9,254,131 B2 * | 2/2016 | Soltz | .................. | A61B 17/0644 |
| 9,289,207 B2 * | 3/2016 | Shelton, IV | ........ | A61B 17/0682 |
| 2003/0035702 A1 | 2/2003 | Lin | | |
| 2003/0201298 A1 * | 10/2003 | Straat | ..................... | B27F 7/21 227/82 |
| 2005/0033329 A1 * | 2/2005 | Bombard | ........... | A61B 17/1152 606/153 |
| 2005/0070935 A1 * | 3/2005 | Ortiz | .................. | A61B 17/1114 606/153 |
| 2005/0075657 A1 * | 4/2005 | Bombard | ........... | A61B 17/1152 606/153 |
| 2005/0131428 A1 * | 6/2005 | Bombard | ........... | A61B 17/1152 606/139 |
| 2005/0242149 A1 * | 11/2005 | Higuchi | ................ | B25C 5/1689 227/2 |
| 2007/0088390 A1 * | 4/2007 | Paz | ................... | A61B 17/06166 606/232 |
| 2007/0118163 A1 * | 5/2007 | Boudreaux | ............ | A61B 17/064 606/157 |
| 2007/0180664 A1 * | 8/2007 | Perry | ....................... | F16L 3/04 24/115 R |
| 2008/0082124 A1 * | 4/2008 | Hess | ................... | A61B 17/064 606/219 |
| 2010/0187285 A1 | 7/2010 | Harris et al. | | |
| 2010/0191255 A1 | 7/2010 | Crainich et al. | | |
| 2010/0191262 A1 | 7/2010 | Harris et al. | | |
| 2010/0191282 A1 | 7/2010 | Harris et al. | | |
| 2012/0228355 A1 * | 9/2012 | Combrowski | ..... | A61B 17/0401 227/175.1 |

\* cited by examiner

WORK HARDENING OF STAPLES WITHIN SURGICAL STAPLER

This application claims priority to U.S. Nonprovisional application Ser. No. 12/782,880 filed on May 19, 2010, which claims priority to U.S. Provisional Patent Application Ser. No. 61/183,376, filed on Jun. 2, 2009, which is herein incorporated by reference in its entirety.

FIELD OF THE INVENTION

The invention generally relates to surgical staplers and stapling.

BACKGROUND

An endocutter is a surgical tool that staples and cuts tissue to transect that tissue while leaving the cut ends hemostatic. An endocutter is small enough in diameter for use in minimally invasive surgery, where access to a surgical site is obtained through a trocar, port, or small incision in the body. A linear cutter is a larger version of an endocutter, and is used to transect portions of the gastrointestinal tract. A typical endocutter receives at its distal end a disposable single-use cartridge with several rows of staples, and includes an anvil opposed to the cartridge. During actuation of an endocutter, the cartridge fires all of the staples that it holds. In order to deploy more staples, the endocutter must be moved away from the surgical site and removed from the patient, after which the old cartridge is exchanged for a new cartridge. The endocutter is then reinserted into the patient. However, it can be difficult and/or time-consuming to located the surgical site after reinsertion. Further, the process of removing the endocutter from the patient after each use, replacing the cartridge, and then finding the surgical site again is tedious, inconvenient and time-consuming, particularly where a surgical procedure requires multiple uses of the endocutter.

In order to overcome these difficulties, Cardica, Inc. of Redwood City, Calif. has developed a true multi-fire endocutter that is capable of firing multiple times without the need to utilize single-use-cartridges. Such an endocutter is described in, for example, U.S. Patent Application Publication No. 2009/0065552, published on Mar. 12, 2009 (the "Endocutter Publication"), which is hereby incorporated by reference herein in its entirety. Referring also to FIG. 1, that endocutter utilizes a feeder belt 2 to which staples 4 are fixed and frangibly separable therefrom. Each staple 4 has a free end 6, and an opposite end 8 that is fixed to the feeder belt 2. Each staple 4 is sheared from the feeder belt 2 at the junction between the end 8 of the staple 4 and the feeder belt 2. The staples 4 are perpendicular to the feeder belt 2 during advancement of the feeder belt 2, deployment of the staples 4, and shearing of the staples 4 from the feeder belt 2.

BRIEF DESCRIPTION OF THE DRAWINGS

The use of the same reference symbols in different figures indicates similar or identical items.

DETAILED DESCRIPTION

Figure 1:
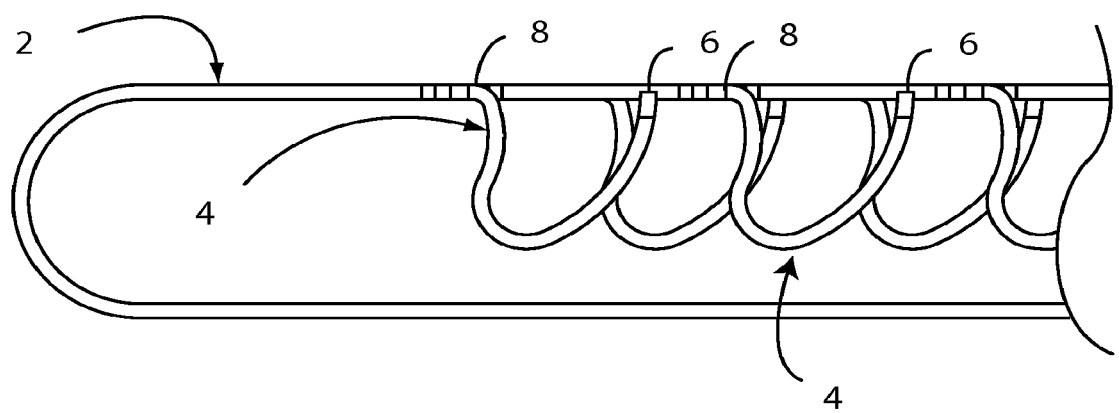
FIG. 1 is a side view of a feeder belt with staples affixed thereto.
Figure 2:
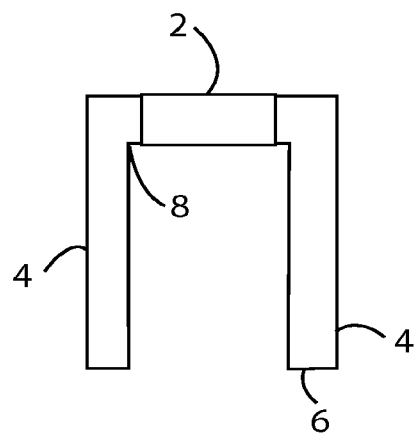
FIG. 2 is an end view of an exemplary feeder belt in a first configuration.

Referring also to FIG. 2, one example of a feeder belt 2 may include at least two surgical staples 4 attached to it, where each staple 4 initially extends downward from the feeder belt 2 at substantially a right angle. The initial orientation of the staples 4 relative to the feeder belt 2 may be different, if desired. Multiple staples 4 may be positioned on each side of the feeder belt 2, where each set of staples 4 is generally aligned in a row, as described in the Endocutter Publication.

One determinant of the location where each staple 4 will break away from the feeder belt 2 during deployment is the tensile strength of the material from which the feeder belt 2 and staples 4 are fabricated. Tensile strength at a particular location may depend on, among other factors, the material from which the feeder belt 2 and staples 4 are fabricated, heat treatment, and work hardening. In the case of 316L stainless steel, for example, the annealed tensile strength is approximately 85 ksi; the tensile strength for 90% cold-worked (i.e., work hardened) 316L stainless steel is as much as 224 ksi. Thus, work hardening a particular area may increase its tensile strength.

Figure 3:
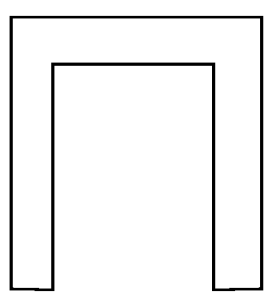
FIG. 3 is an end view of a passage in a surgical tool in which the feeder belt of FIG. 2 is received.

As one example, it may be desirable to anneal the feeder belt 2 and staples 4, then work harden the end 8 of the staple 4 attached to the feeder belt 2 and/or the portion of the feeder belt 2 to which that end 8 of the staple 4 is fixed. In this way, the softer, annealed portion of the staple 4 bends first during deployment in response to a first force, and the staple 4 is sheared from the feeder belt 2 in response to a second force greater than the first force. The junction between the feeder belt 2 and one or more staples 4 can be work hardened in a surgical tool in any suitable manner. As one example, referring to FIG. 3, the feeder belt 2 and staples 4 may be fed through a channel 10 defined in a surgical tool, where the shape of the channel 10 corresponds to the initial shape of the combined feeder belt 2 and staples 4. The channel 10 may change shape along its longitudinal direction (the direction perpendicular to the printed page). For example, referring to FIG. 4, the channel 10 may change shape to one in which the lateral portions of the channel 10 are angled outward. The channel 10 shaped as in FIG. 4—or any channel 10 shaped differently from the initial configuration of the channel 10 may be referred to as a forming station. As the feeder belt 2 is pulled longitudinally through the channel 10, it passes through the channel 10 as configured in FIG. 3. The channel 10 changes shape gradually until it reaches the shape of FIG. 4. Thus, as the feeder belt 2 is pulled longitudinally through the channel 10 into the forming station of FIG. 4, the staples 4 fixed to the feeder belt 2 are gradually bent outward relative to the feeder belt 2, where that bending is localized at the junction between each staple 4 and the feeder belt 2. That is, contact between the staples 4 and the bent-outward lateral portions of channel 10 causes those staples 4 to bend outward as well, as seen in FIG. 5. The channel 10 then gradually changes shape back to the configuration of FIG. 2, and the angle of the staples 4 relative to the feeder belt 2 returns to substantially the same angle as in the initial configuration of FIG. 2 as well. In this way, the junction between each staple 4 and the feeder belt 2 may be work hardened in the surgical tool. This work hardening may be considered the final step of manufacturing the staples 4.

Figure 4:
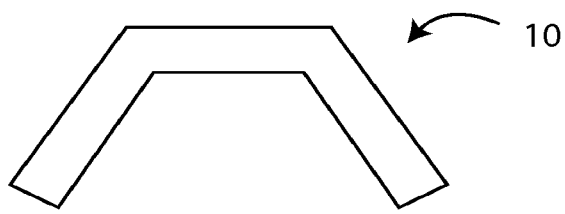
FIG. 4 is an end view of a forming station within a surgical tool in which the feeder belt of FIG. 2 is received and through which the feeder belt 2 is movable.
Figure 5:
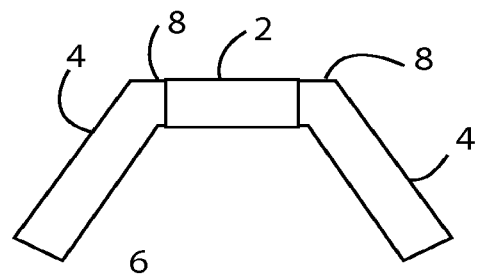
FIG. 5 is an end view of the exemplary feeder belt of FIG. 2 in a second configuration.

Alternately, the shape of the forming station of FIG. 4 may be different in order to increase or decrease bending of the staples 4 relative to the feeder belt 2, and thus increase or decrease the amount of work hardening at the junction between each staple 4 and the feeder belt 2. Alternately, the shape of the forming station of FIG. 4 may be different in order to concentrate bending in, and work harden, a different location in the feeder belt 2 and/or staples 4. Alternately, more than one forming station may be used, in order to work harden different locations in the feeder belt 2 and/or staples 4 each time, and/or to repeat one or more previous bends in order to further cold work a particular region.

Deployment and closure of the staples 4 otherwise may be performed substantially as set forth in the Endocutter Publication. While the present invention has been described with respect to the particular example of a feeder belt 2 and surgical staples 4 fixed to and frangibly separable from that feeder belt 2, it will be appreciated that the use of one or more forming stations, or any other structure or mechanism for cold working a part within a tool, may be used to alter the tensile strength of that part at a selected local area.

While the invention has been described in detail, it will be apparent to one skilled in the art that various changes and modifications can be made and equivalents employed, without departing from the present invention. It is to be understood that the invention is not limited to the details of construction, the arrangements of components, and/or the steps of performing anastomosis set forth in the above description or illustrated in the drawings. Therefore, the invention is not to be restricted or limited except in accordance with the following claims and their legal equivalents.

What is claimed is:

1. A method of forming a break away section on a first surgical staple that is attached to a row of surgical staples at a first junction, the method comprising the steps of:
    loading the row of surgical staples into a surgical stapler;
    moving the row of surgical staples in a longitudinal direction relative to the surgical stapler;
    contacting the first surgical staple with a first interior part of the surgical stapler as the row moves relative to the surgical stapler;
    bending the first surgical staple at the first junction in response to contact with the first interior part of the surgical stapler; and
    continuing said bending of the first surgical staple in at the first junction until the first junction is work hardened to form said break away section at the first junction; and
    stapling tissue with the surgical stapler.

2. The method of claim 1, wherein the first interior part of the surgical stapler comprises at least one forming station.

3. The method of claim 1, wherein the first interior part of the surgical stapler comprises a plurality of forming stations.

4. The method of claim 1, further comprising the step of shearing the first surgical staple from the row of surgical staples at the first junction.

5. The method of claim 4, wherein the step of shearing the first surgical staple from the row of surgical staples comprises the step of contacting the first surgical staple with a second interior part of the surgical stapler as the row moves relative to the surgical stapler.

6. The method of claim 5, wherein the first surgical staple receives a first contact force from the first interior part and receives a second contact force from the second interior part that is greater than the first contact force.

7. The method of claim 1, wherein the row of surgical staples comprises a second surgical staple attached to the row at a second junction.

8. The method of claim 7, further comprising the step of bending the second surgical staple at the second junction until the second junction is work hardened to form a second break away section at the second junction.

9. The method of claim 8, wherein the break away section is formed on the first surgical staple before the second break away section is formed on the second surgical staple.

10. The method of claim 8, wherein the second surgical staple is bent at said second junction in response to contact with the first interior part of the surgical stapler.

11. The method of claim 8, further comprising the step of shearing the second surgical staple from the row of surgical staples at the first junction.

12. The method of claim 11, wherein the step of shearing the second surgical staple from the row of surgical staples comprises the step of contacting the second surgical staple with the second interior part of the surgical stapler as the row moves relative to the surgical stapler.

13. The method of claim 12, wherein the first surgical staple is sheared from the row of surgical staples before the second surgical staple is sheared from the row of surgical staples.

14. The method of claim 1, further comprising the step of using the surgical stapler in a surgical procedure.

15. The method of claim 1, further comprising the step of inserting the surgical stapler in a patient.

16. The method of claim 1, further comprising the step of moving the surgical stapler to a surgical site.

17. The method of claim 1, further comprising the step of transecting a tissue.

\* \* \* \* \*